(12) United States Patent
Ruschel et al.

(10) Patent No.: US 11,439,835 B2
(45) Date of Patent: Sep. 13, 2022

(54) ASSEMBLY FOR A HEADER, HEADER, AND IMPLANT COMPRISING THE HEADER, AND METHOD FOR MOUNTING A HEADER

(71) Applicant: BIOTRONIK SE & CO. KG, Berlin (DE)

(72) Inventors: Marina Ruschel, Berlin (DE); Kathy Hartmann-Bax, Nuthe-Urstromtal (DE)

(73) Assignee: BIOTRONIK SE & Co. KG, Berlin (DE)

( * ) Notice: Subject to any disclaimer, the term of this patent is extended or adjusted under 35 U.S.C. 154(b) by 54 days.

(21) Appl. No.: 16/519,599

(22) Filed: Jul. 23, 2019

(65) Prior Publication Data
US 2020/0038666 A1 Feb. 6, 2020

(30) Foreign Application Priority Data
Aug. 2, 2018 (EP) .................................... 18187094

(51) Int. Cl.
*A61N 1/375* (2006.01)
*A61N 1/372* (2006.01)
*H01R 12/59* (2011.01)

(52) U.S. Cl.
CPC ....... *A61N 1/3754* (2013.01); *A61N 1/37229* (2013.01); *A61N 1/37512* (2017.08); *H01R 12/592* (2013.01)

(58) Field of Classification Search
CPC .............. A61N 1/3754; A61N 1/37229; A61N 1/37512; A61N 1/3956; A61N 1/3752; A61N 1/362; H01R 12/592; H01R 13/405; H01R 24/58; H01R 2201/12
See application file for complete search history.

(56) References Cited

U.S. PATENT DOCUMENTS

| 7,537,474 | B2 | 5/2009 | Deininger et al. | |
|---|---|---|---|---|
| 8,065,009 | B2 | 11/2011 | Biggs | |
| 2006/0089682 | A1* | 4/2006 | Kronich | H01R 12/592 607/37 |
| 2007/0087637 | A1* | 4/2007 | Zart | H01R 13/504 439/736 |
| 2007/0099518 | A1* | 5/2007 | Arnholt | A61N 1/3752 439/675 |
| 2011/0190833 | A1* | 8/2011 | Ries | A61N 1/375 607/2 |
| 2011/0293866 | A1* | 12/2011 | Specht | A61N 1/3752 428/35.7 |

(Continued)

FOREIGN PATENT DOCUMENTS

EP 2082780 A2 7/2009
WO 2009009299 A1 1/2009

*Primary Examiner* — Catherine M Voorhees
(74) *Attorney, Agent, or Firm* — Laurence A. Greenberg; Werner H. Sterner; Ralph E. Locher

(57) ABSTRACT

An assembly for an electrode connection device of an implant has a continuous receiving unit for a plug, a first connecting element which is arranged in a front region of the receiving unit and has at least two flat lateral surfaces, and a second connecting element, which is arranged in a rear region of the receiving unit. The second connecting element includes at least two flat lateral surfaces. Furthermore, an electrode connection device, an implant, and a method for mounting an electrode connection device all utilize the assembly.

11 Claims, 5 Drawing Sheets

(56) References Cited

U.S. PATENT DOCUMENTS

| | | | |
|---|---|---|---|
| 2012/0215288 A1* | 8/2012 | Zhang | A61N 1/3754 |
| | | | 607/72 |
| 2012/0245664 A1* | 9/2012 | Smith | H01R 13/111 |
| | | | 607/117 |
| 2015/0094792 A1 | 4/2015 | Kane et al. | |
| 2017/0266451 A1 | 9/2017 | Lim et al. | |
| 2017/0279238 A1* | 9/2017 | Spadgenske | H01R 43/005 |
| 2017/0281951 A1* | 10/2017 | Janzig | H01R 13/42 |
| 2018/0028820 A1* | 2/2018 | Nageri | H01R 13/2421 |
| 2018/0289968 A1* | 10/2018 | Lopez | A61N 1/36071 |
| 2019/0117962 A1* | 4/2019 | Chiang | A61N 1/3752 |
| 2020/0001095 A1* | 1/2020 | Iyer | A61N 1/3787 |
| 2020/0008900 A1* | 1/2020 | Henschel | A61B 90/94 |

\* cited by examiner

ASSEMBLY FOR A HEADER, HEADER, AND IMPLANT COMPRISING THE HEADER, AND METHOD FOR MOUNTING A HEADER

CROSS-REFERENCE TO RELATED APPLICATION

This application claims the priority, under 35 U.S.C. § 119, of European application EP 18187094.0, filed Aug. 2, 2018; the prior application is herewith incorporated by reference in its entirety.

BACKGROUND OF THE INVENTION

Field of the Invention

The disclosure relates to an assembly for an electrode connection device (also referred to as a header), to an electrode connection device, to an implant comprising the electrode connection device, and to a method for mounting an electrode connection device on an implant.

Previously, headers for active implants have been composed of a large number of individual components. It is important that the components are exactly aligned with each other before being casted with a resin to form the header. This procedure is very complex.

U.S. patent publication No. 2017/0266451 A1 discloses a header including a modular feedthrough.

U.S. patent publication No. 2017/0279238 A1 discloses a header including a prefabricated header module.

Another header is described in international patent document WO 2009/009299 A1, corresponding to U.S. Pat. No. 7,537,474.

SUMMARY OF THE INVENTION

It is the objective of the invention to provide improved technologies for implants. In particular, the production of the electrode connection device is to be simplified.

An assembly for an electrode connection device of an implant, an electrode connection device, an implant, and a method for forming an electrode connection device on an implant are disclosed. Further embodiments are the subject matter of dependent claims.

An assembly for an electrode connection device of an implant is provided. The assembly comprises a continuous receiving unit for a plug. Furthermore, a first connecting element is provided, which is arranged in a front region of the receiving unit, wherein the first connecting element includes at least two flat lateral surfaces. Finally, a second connecting element is provided, which is arranged in a rear region of the receiving unit, wherein the second connecting element includes at least two flat lateral surfaces.

Furthermore, an electrode connection device for an implant comprising an assembly disclosed herein is provided.

The disclosure further includes an implant comprising an electrode connection device and an assembly.

The electrode connection device can also be referred to as a connecting head or header.

The flat lateral surfaces enable an at least partially angular shape and allow the assembly to be easily gripped (manually or automatically). In this way, automation of the production process can be realized.

The assembly can be surrounded by a plastic material at least in sections. For example, the assembly can be overmolded with the plastic material in sections. The plastic material can be a thermoplastic material, such as polysulfone. It is also possible to use a biocompatible casting resin. The plastic material can provide additional stability to the assembly. It is thus possible to produce the assembly as a prefabricated component, which is subsequently processed to form an electrode connection device of an implant.

A connecting region of the first connecting element can be free of plastic material. As an alternative or in addition, a connecting region of the second connecting element can be free of plastic material.

A first guide for a first conductor for connection to the connecting region of the first connecting element can be formed in the plastic material and/or a second guide for a second conductor for connection to the connecting region of the second connecting element can be formed in the plastic material.

The first guide can be formed so as to adjoin the connecting region of the first connecting element and/or the second guide can be formed so as to adjoin the connecting region of the second connecting element.

A first conductor (second conductor) can be connected to the connecting region of the first connecting element (of the second connecting element) so as to enable a connection from a plug that is inserted into the receiving unit to an implant. The connecting region of the first connecting element and/or the connecting region of the second connecting element can be designed as planar elements. The connecting region of the first connecting element and/or the connecting region of the second connecting element can be circular and, for example, have diameters of 1 to 5 mm. In this way, a large welding area for attaching the first conductor and/or the second conductor is provided. In one embodiment, both the first guide and the second guide are formed so as to adjoin the respective connecting regions. The guides allow the conductors to be connected to the respective connecting regions, without causing a short circuit.

It may be provided that the first connecting element and the second connecting element are arranged offset from one another. In other words, the first connecting element and the second connecting element are located on two different planes. The differing arrangement facilitates the connection of the conductors to the connecting elements, without the conductors making contact with one another.

In one embodiment, the assembly can comprise an antenna, wherein the antenna has a U-shaped form in an intermediate region, which is formed between the first connecting element and the second connecting element. The intermediate region can be narrower than the abutting connecting elements. Together with the U-shaped form of the antenna, a gripping recess for an automatic gripper is thus formed.

A positioning unit can be formed at a rear end of the receiving unit. The positioning unit can be formed as an angled structure and, for example, form a right angle relative to the receiving unit. The positioning unit can be made of the plastic material and, for example, be formed in one piece with the plastic coating of the assembly. During the arrangement of the assembly in a receptacle, the positioning unit can be arranged on a housing of the implant to facilitate the alignment of the assembly. The positioning unit can have a tapered end.

The assembly can comprise a further receiving unit for a further plug, wherein a third connecting element is arranged in a front region of the further receiving unit, and wherein a fourth connecting element is arranged in a rear region of the further receiving unit. The explanations provided herein with respect to the receiving unit apply analogously to the further receiving unit. Moreover, the explanations made with respect to the first connecting element and the second connecting element apply analogously to the third connecting element and the fourth connecting element.

According to a further aspect, a method for forming an electrode connection device on an implant is disclosed. The method comprises the following steps:

a) providing an assembly, comprising:
   a1)—a continuous receiving unit for a plug;
   a2) a first connecting element, which is arranged in a front region of the receiving unit, wherein the first connecting element includes at least two flat lateral surfaces; and
   a3) a second connecting element, which is arranged in a rear region of the receiving unit, wherein the second connecting element includes at least two flat lateral surfaces;
b) arranging and attaching a spring element in the receiving unit;
c) sealing openings of the receiving unit using casting aids;
d) attaching a first conductor to the first connecting element;
e) attaching a second conductor to the second connecting element;
f) arranging the assembly on a housing of the implant;
g) connecting the first conductor to a feedthrough which is formed on a housing;
h) connecting the second conductor to the feedthrough;
i) arranging the assembly, together with the housing, in a casting mold;
j) filling the casting mold with a synthetic resin; and
k) after the synthetic resin has cured, removing the casting aids.

The method can comprise the additional steps:

l) arranging and attaching an antenna on the assembly; and
m) connecting the antenna to the feedthrough, wherein the further steps are carried out before the assembly is arranged on the housing.

Furthermore, it may be provided that possibly protruding resin is removed after curing, for example by means of grinding and/or polishing.

The casting mold can be a silicone mold.

The feedthrough can comprise one or more plug contacts (such as pins) for the connection of the conductors and/or the antenna.

The synthetic resin can be an epoxy resin. Epoxy resins are synthetic resins that carry epoxide groups. These are curable resins (reaction resins), which can be reacted with a hardener or curing agent and optionally further additives to yield a thermoset plastic material. Epoxy resins are polyethers including two terminal epoxide groups. The hardening or curing agents are reactants and form, together with the resin, a macromolecular plastic material.

The synthetic resin can adhere directly to the housing of the implant, so that an additional adhesion promoter is not required. In other words, the contact surface between the cured synthetic resin and the housing of the implant can be free of an adhesion promoter. The housing of the implant can be made of titanium.

The electrode connection device can be a header for an implantable cardiac pacemaker or an implantable cardioverter defibrillator (ICD). In this case, the electrode connection device is used to electrically connect one or more electrode leads to the implant.

The features disclosed in connection with the assembly and the electrode connection device can be applied analogously to the method, and vice versa.

Other features which are considered as characteristic for the invention are set forth in the appended claims.

Although the invention is illustrated and described herein as embodied in an assembly for a header, a header, and an implant comprising the header, and a method for mounting a header, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
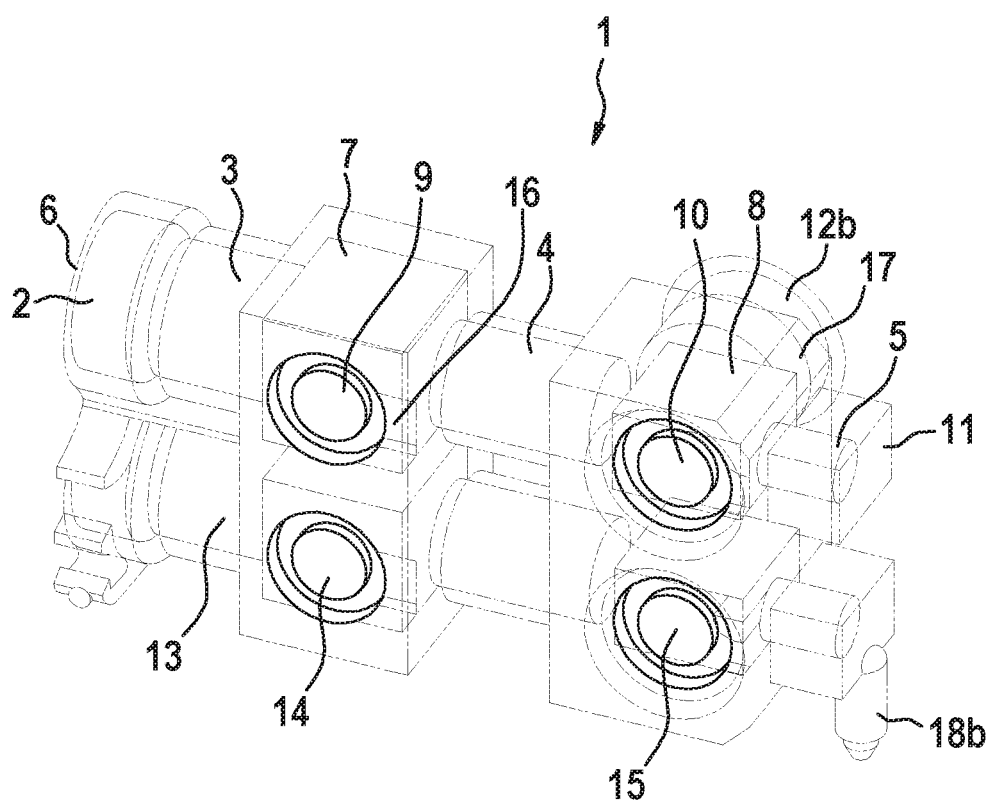
FIG. 1 is a diagrammatic, perspective view of an embodiment of an assembly for an electrode connection device.

Hereafter, the same reference numerals are used for identical components.

FIGS. 1 to 7 show the individual steps for mounting an electrode connection device (header) on an implant. The steps are described in more detail hereafter.

Referring now to the figures of the drawings in detail and first, particularly to FIG. 1 thereof, there is shown an assembly 1 (also referred to as header core) comprising a first receiving unit 2 for an electrode plug and a second receiving unit 13 for a further electrode plug. The first receiving unit 2 has a front opening 6 through which the electrode plug can be inserted. The first receiving unit 2 comprises a first section 3, a second section 4 and a third section 5. The diameter of the first section 3 is larger than the diameter of the second section 4. The diameter of the second section 4, in turn, is larger than the diameter of the third section 5. In other words, the first receiving unit 2 becomes incrementally narrower from the front opening 6 to the end.

A first connecting element 7 is formed between the first section 3 and the second section 4 (that is, in a front region of the first receiving unit 2). A second connecting element 8 is formed between the second section 4 and the third section 5 (in a rear region of the first receiving unit 2). Both the first connecting element 7 and the second connecting element 8 comprise at least two flat lateral surfaces. This allows easy gripping of the assembly 1 during assembly and enables automation of the assembly steps. In the shown embodiment, the first connecting element 7 and the second connecting element 8 have a substantially cuboid design. The second connecting element 8 comprises a chamfered edge 17, which serves material savings purposes and compliance to the flow direction of the epoxy resin. A recess 12a is formed in the plastic coating on a rear side of the first connecting element 7. A rear opening 12b is formed on a rear side of the second connecting element 8.

The assembly is partially surrounded by a plastic material 11. In the shown embodiment, the assembly is partially overmolded with polysulfone. Recesses are formed in the plastic material 11 for a first contact surface 9 and a second contact surface 10. The first and second contact surfaces are designed as circular areas. Adjoining the first and second contact surfaces 9, 10, a respective guide 16 is formed. The guide 16 is used to receive a connecting element (such as a wiring strip). The guides at the contact surfaces prevent connecting elements of different contact surfaces from making contact with one another.

The second receiving unit 13 is designed analogously to the first receiving unit 2. For the sake of clarity, the components of the second receiving unit (one opening, the three incrementally narrowing sections and the two connecting elements) are not denoted by reference numerals. The second receiving unit 13 likewise comprises two contact surfaces (third contact surface 14 and fourth contact surface 15) for connections. Adjoining the contact surfaces, guides are formed.

A positioning unit 18b, which is designed as a pin having a tapered end, is formed at one end of the second receiving unit. When the assembly 1 is mounted on a housing 29 (see FIG. 4), the pointed end of the positioning unit 18b can be inserted in a receptacle of the housing so as to facilitate the arrangement of the assembly on the housing with precise fit. However, the assembly can also be implemented without the positioning unit 18b.

Figure 2A:
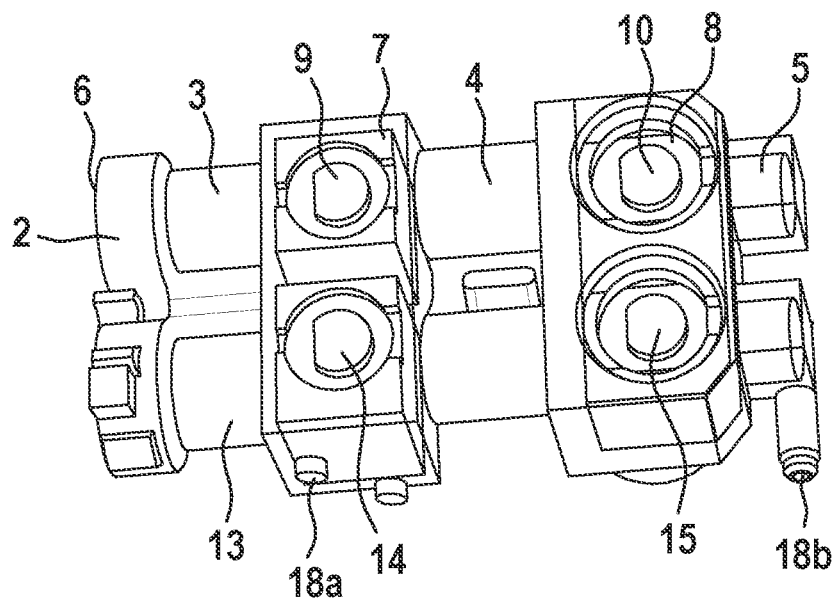
FIG. 2A is a front, perspective view of the assembly according to FIG. 1.
Figure 2B:
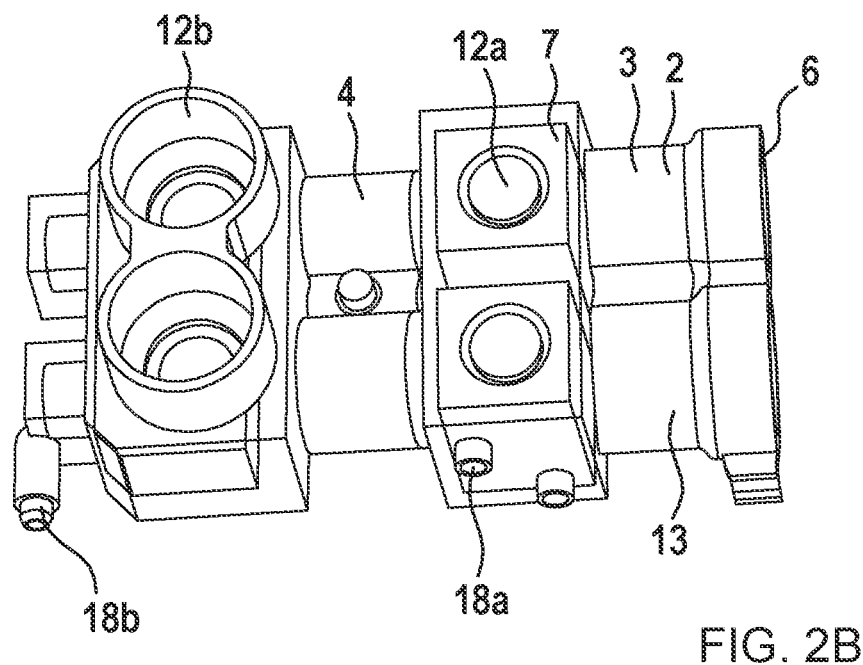
FIG. 2B is a rear, perspective view of the assembly according to FIG. 1.

On a bottom side of the assembly, positioning pins 18a are formed (see FIGS. 2A-2B). The positioning pins can be arranged in associated receptacles when the assembly is arranged on the housing of the implant. The shown embodiment shows two positioning pins; however, other quantities of positioning pins are likewise possible.

The first receiving unit 2 and the second receiving unit 13 each comprise a spring sleeve and a receiving portion for a plug. The first receiving unit 2 and the second receiving unit 13 can be designed as IS-1 connectors.

Figure 3B:
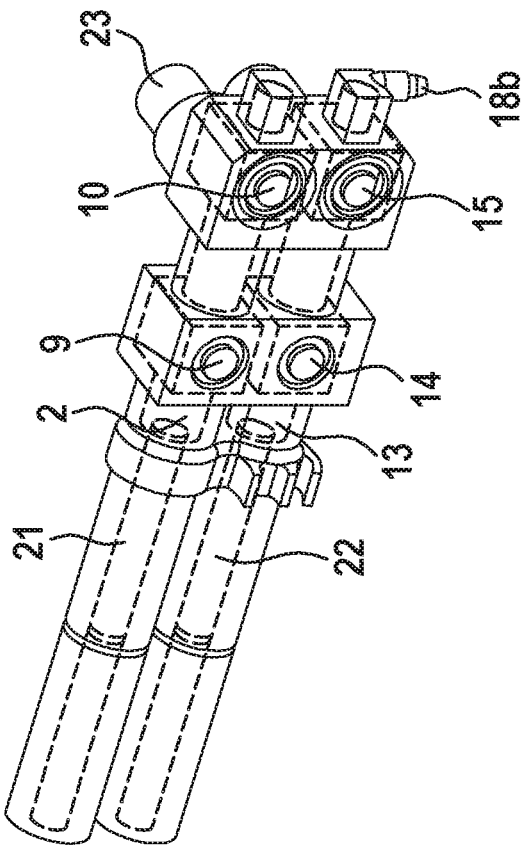
FIG. 3B is a rear, perspective view of the assembly according to FIG. 1 with casting aids.
Figure 3A:
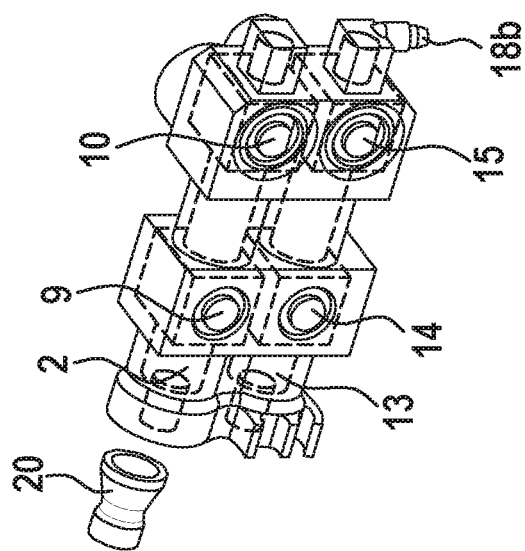
FIG. 3A is a front, perspective view of the assembly according to FIG. 1 with casting aids.

A spring element 20 is arranged in the first receiving unit 2 and attached there (FIG. 3A). The recess 12a in the plastic material is used to weld the spring element 20 that is arranged inside the first receiving unit 2 into the first connecting element 7 by resistance welding. A further spring element is arranged and attached analogously in the second receiving unit 13 (not shown). The openings of the assembly 1 are subsequently closed and sealed with potting aids 21, 22, 23 (FIG. 3B).

Figure 4:
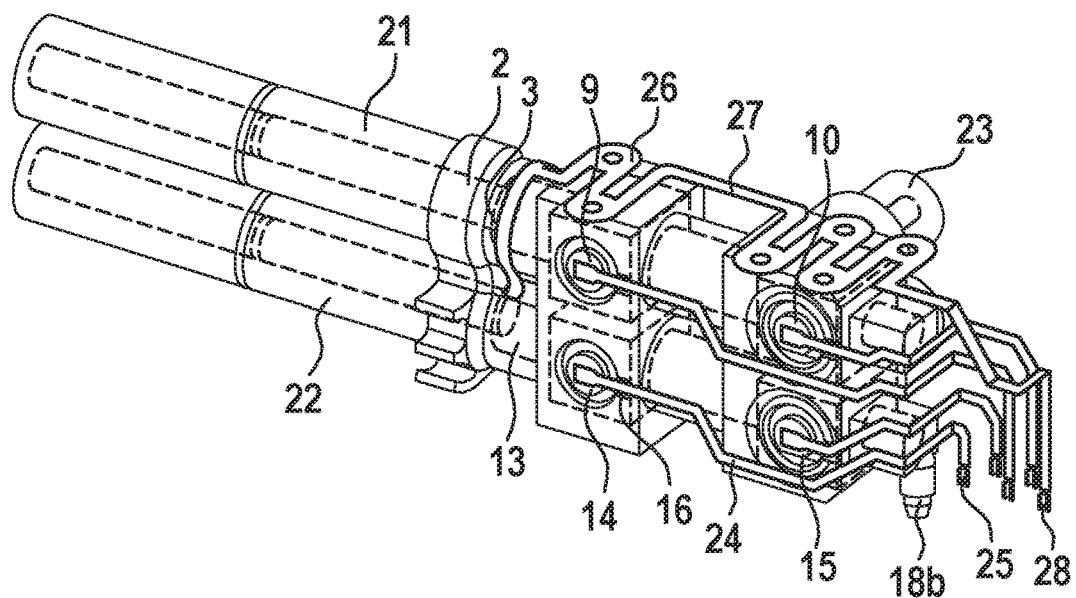
FIG. 4 is a perspective view showing the assembly according to FIGS. 1 to 3 including an antenna and conductors.
Figure 5:
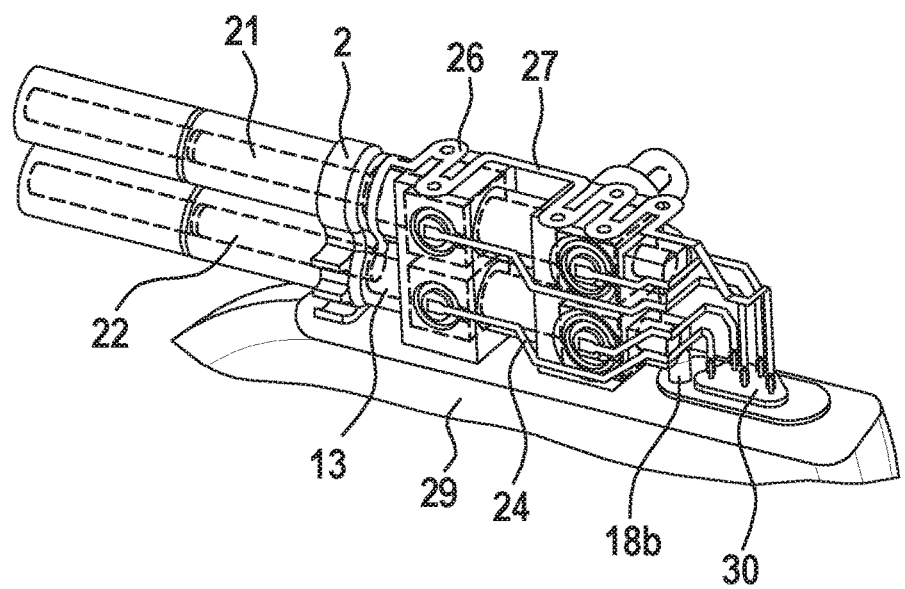
FIG. 5 is a perspective view showing the assembly according to FIGS. 1 to 4 arranged on a housing.
Figure 6:
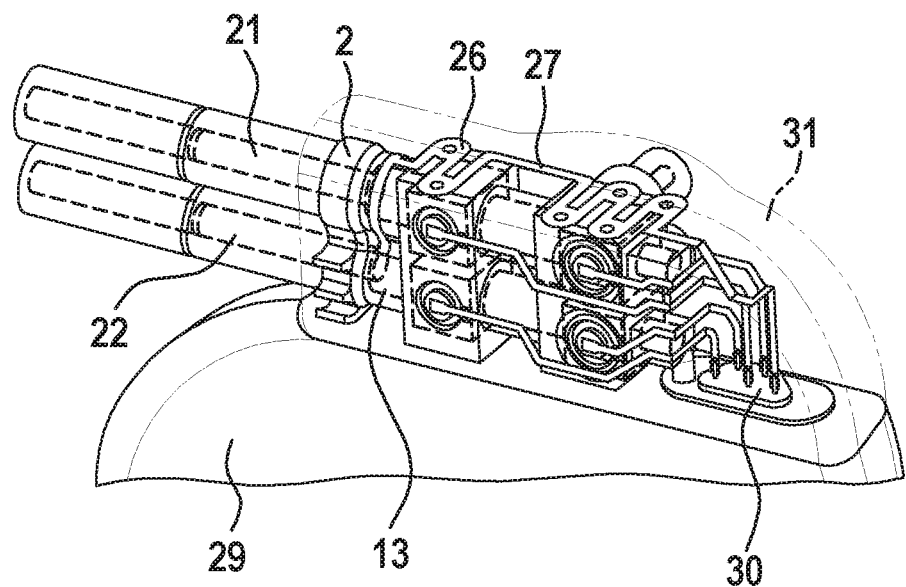
FIG. 6 is a perspective view showing the assembly according to FIGS. 1 to 5 when completely casted (with casting aids)

FIG. 4 shows another assembly step. A wire band 24 is attached to the third contact surface 14 (such as welded). At the rear end, the wire band 24 includes a wire band connection 25, which can be connected to a pin contact of a feedthrough 30 (see FIG. 5) and placed onto the pin contact, for example. Further wire bands are connected to the other contact surfaces 9, 10, 15.

An antenna 26 is attached to the assembly 1. The antenna 26 partially encloses the first section 3 of the first receiving unit 2 and is clipped thereto. In a region between the first connecting element 7 and the second connecting element 8, the antenna 26 comprises a U-shaped section 27. In this way, a gripping recess is formed, which can be used, for example, together with an automated gripper to hold and transport the assembly. At a rear end of the antenna, an antenna connection 28 is formed for connection to the feedthrough 30.

The assembly including the wire bands and the antenna is subsequently arranged in a non-illustrated casting mold (such as a silicone mold). The wire band connections and the antenna connection 28 are placed onto assigned pins of the feedthrough 30 and connected to the pins (such as welded). The casting mold is closed and filled with a synthetic resin 31 (such as epoxy resin). In this way, the electrode connection device is molded (see FIG. 6).

Figure 7:
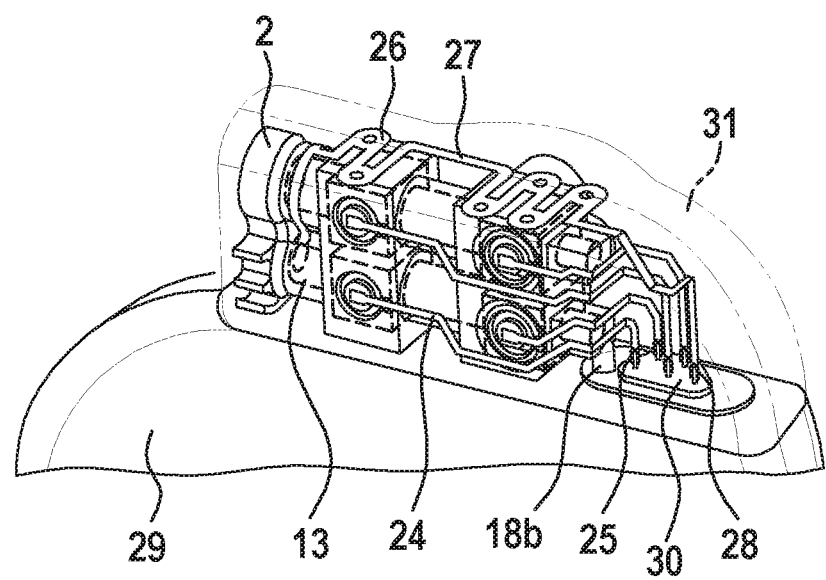
FIG. 7 is a perspective view showing the assembly according to FIGS. 1 to 5 completely casted (without casting aids).

The casting aids 21, 22, 23 are removed and possibly excess resin on the outer surfaces is removed, such as by means of grinding and/or polishing. The implant comprising the electrode connection device is thus fully assembled (FIG. 7).

The assembly/electrode connection device can have the following advantages:

a) no penetration of resin and/or other particles into the first (and optionally second) receiving unit, so that no rework is required;

b) insulating distances of the wire bands are predefined by the design of the assembly, so that the risk of an electrical short circuit is reduced or even precluded;

c) the design enables automated production of the electrode connection device; and d) compared to the previously known production, manufacturing steps are eliminated, resulting in a shorter manufacturing time.

The features disclosed in the description, the claims and the figures can be relevant for the implementation of embodiments either alone or in any random combination with one another.

When reading the claim language, the following definitions apply. When the claim language recites A and/or B it means A alone, B alone or A and B. When the claim language recites at least one of A and B it means A alone, B alone or A and B. When the claim language recites at least one of A or B it means A alone, B alone or A and B.

The following is a summary list of reference numerals and the corresponding structure used in the above description of the invention:

1 assembly
2 first receiving unit
3 first section of the first receiving unit
4 second section of the first receiving unit
5 third section of the first receiving unit
6 front opening
7 first connecting element
8 second connecting element
9 first contact surface
10 second contact surface
11 plastic material
12a recess
12b rear opening
13 second receiving unit
14 third contact surface
15 fourth contact surface
16 guide
17 chamfered edge
18a positioning pins 18b positioning unit
20 spring element
21 first casting aid
22 second casting aid
23 third casting aid
24 wire band
25 wire band connection
26 antenna
27 U-shaped section of the antenna
28 antenna connection
29 housing
30 feedthrough
31 resin

The invention claimed is:

1. An assembly for an electrode connection device of an implant, the assembly comprising:
a continuous receiving unit for receiving a plug in a first direction and having a first section with a first diameter, a second section with a second diameter and a third section with a third diameter, said first diameter being larger than said second diameter and said second diameter being larger than said third diameter;
a first connector disposed in a front region of said continuous receiving unit between said first section and said second section, said first connector having at least two flat lateral surfaces;
a second connector disposed in a rear region of said continuous receiving unit between said second section and said third section, said second connector having at least two flat lateral surfaces; and
a plastic material directly surrounding and coming into contact with said first connector and said second connector and forming parts of said first section, said second section and said third section, said plastic material having a recess formed therein directly adjacent one of said at least two flat lateral surfaces of said first connector, and said recess running in a second direction being perpendicular to said first direction.

2. The assembly according to claim 1, wherein:
said first connector having a connecting region being free of said plastic material; and/or
said second connector having a connecting region being free of said plastic material.

3. The assembly according to claim 2, wherein:
said plastic material having a first guide formed therein for a first conductor for connection to said connecting region of said first connector; and/or
said plastic material having a second guide formed therein for a second conductor for connection to said connecting region of said second connector.

4. The assembly according to claim 3, wherein:
said first guide is formed so as to adjoin said connecting region of said first connector; and/or
said second guide is formed so as to adjoin said connecting region of said second connector.

5. The assembly according to claim 1, wherein said first connector and said second connector are disposed offset from one another.

6. The assembly according to claim 1, further comprising an antenna having a U-shaped form in an intermediate region, and is formed between said first connector and said second connector.

7. The assembly according to claim 1, further comprising a positioning unit formed at a rear end of said continuous receiving unit.

8. The assembly according to claim 1, further comprising:
a further receiving unit for receiving a further plug;
a third connector disposed in a front region of said further receiving unit; and
a fourth connector disposed in a rear region of said further receiving unit.

9. An electrode connection device for an implant, comprising:
an assembly, containing:
a continuous receiving unit for receiving a plug in a first direction and having a first section with a first diameter, a second section with a second diameter and a third section with a third diameter, said first diameter being larger than said second diameter and said second diameter being larger than said third diameter;
a first connector disposed in a front region of said continuous receiving unit between said first section and said second section, said first connector having at least two flat lateral surfaces;
a second connector disposed in a rear region of said continuous receiving unit between said second section and said third section, said second connector having at least two flat lateral surfaces; and
a plastic material directly surrounding and coming into contact with said first connector and said second connector and forming parts of said first section, said second section and said third section, said plastic material having a recess formed therein directly adjacent one of said at least two flat lateral surfaces of said first connector, and said recess running in a second direction being perpendicular to said first direction.

10. The electrode connection device for an implant according to claim 9, wherein said assembly is overmolded with a synthetic resin.

11. An implant, comprising:
an electrode connection device having an assembly, said assembly containing:
a continuous receiving unit for receiving a plug in a first direction and having a first section with a first diameter, a second section with a second diameter and a third section with a third diameter, said first diameter being larger than said second diameter and said second diameter being larger than said third diameter;
a first connector disposed in a front region of said continuous receiving unit between said first section and said second section, said first connector having at least two flat lateral surfaces;
a second connector disposed in a rear region of said continuous receiving unit between said second section and said third section, said second connector having at least two flat lateral surfaces:
a plastic material directly surrounding and coming into contact with said first connector and said second connector and forming parts of said first section, said second section and said third section, said plastic material having a recess formed therein directly adjacent one of said at least two flat lateral surfaces of said first connector, and said recess running in a second direction being perpendicular to said first direction; and
a synthetic resin surrounding said assembly and said plastic material.

* * * * *